United States Patent

Baroni et al.

[11] Patent Number: 5,286,734
[45] Date of Patent: Feb. 15, 1994

[54] ARYLPIPERIDINE DERIVATIVE, PROCESS FOR THE PREPARATION THEREOF AND PHARMACEUTICAL COMPOSITIONS CONTAINING IT

[75] Inventors: Marco Baroni, Vanzago; Umberto Guzzi, Milan, both of Italy; Michèle Arnone, Ramonville St Agne; Philippe Soubrie, Saint Mathieu de Treviers, both of France

[73] Assignee: Elf Sanofi, Paris, France

[21] Appl. No.: 49,106

[22] Filed: Apr. 16, 1993

[30] Foreign Application Priority Data

Apr. 17, 1992 [FR] France .................... 92 04821

[51] Int. Cl.[5] .................. A61K 31/445; C07D 211/06
[52] U.S. Cl. ......................... 514/319; 546/205
[58] Field of Search ................. 514/319; 546/205

[56] References Cited

U.S. PATENT DOCUMENTS

| | | | |
|---|---|---|---|
| 3,910,930 | 10/1975 | Cavalla | 514/319 |
| 4,521,428 | 6/1985 | Nisato et al. | 514/277 |
| 4,563,466 | 1/1986 | Archibald | 514/319 |
| 4,921,863 | 5/1990 | Sugimoto | 514/319 |
| 5,026,716 | 6/1991 | Bianchetti et al. | 514/336 |
| 5,109,005 | 4/1992 | Croci et al. | 514/277 |

FOREIGN PATENT DOCUMENTS

| | | |
|---|---|---|
| 0372776 | 6/1990 | European Pat. Off. . |
| 0458696 | 11/1991 | European Pat. Off. . |
| 0458697 | 11/1991 | European Pat. Off. . |
| 2083476 | 3/1982 | United Kingdom . |

Primary Examiner—C. Warren Ivy
Assistant Examiner—Celia Chang
Attorney, Agent, or Firm—Bacon & Thomas

[57] ABSTRACT

A compound of formula

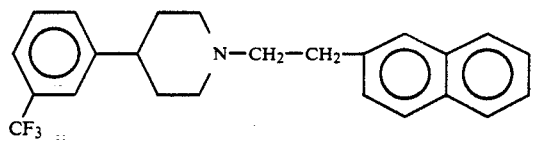

and its acid addition salts are useful in the treatment of sexual dysfunctions in male mammals.

5 Claims, No Drawings

ARYLPIPERIDINE DERIVATIVE, PROCESS FOR THE PREPARATION THEREOF AND PHARMACEUTICAL COMPOSITIONS CONTAINING IT

The present invention relates to a new piperidine derivative as well as its acid addition salts, the process for the preparation thereof and the pharmaceutical compositions containing it.

Several piperidine derivatives are known in the art. In particular, British patent application GB-A-2083476 claims 4-aryl-piperidines or -tetrahydropyridines endowed with psychotropic and dopamine agonist activity of formula (A)

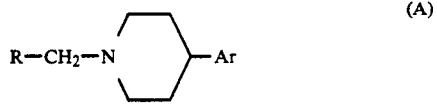

wherein the dotted line represents a carbon-carbon bond or nothing, R represents an indol-3-yl, naphth-1-yl, naphth-2-yl, or benzothien-3-yl group and Ar represents an optionally substituted phenyl group.

International patent application WO-A-89/11476 claims antipysochotic 2-aminothiazoles which may be substituted with an arylpiperidinoethyl group.

European patent application EP-A-0372776 describes N-alkyl-arylpiperidines with antipsychotic activity wherein the alkyl group linked to the nitrogen atom bears a phenyl, substituted phenyl or heteroaryl substituent.

International patent application WO-A-91/09594 claims the use of a large class of compounds which includes N-arylalkyl- or N-heteroaryl-alkyl 4-arylpiperidines for the treatment of schizophrenia and other psychoses.

Finally, European patent EP-B-101381 describes and claims 4-(3-trifluoromethylphenyl)-1,2,3,6-tetrahydropyridine derivatives with anorexigenic activity including the compound of following formula (B)

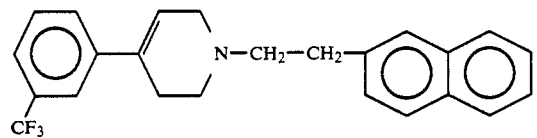

Other, different therapeutical applications of the above compound (B) have been claimed in the following European patent applications: EP-A-0369887 (use in anxiodepressive disorders), EP-A-0412901 (use in intestinal motility disorders) and EP-A-0458696 (use in cerebral and neuronal disorders).

It has now been found that the compound of following formula (I)

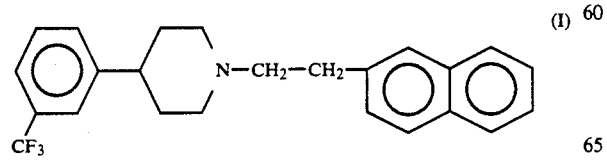

which differs from the compound of formula (B) in the absence of the double bond in the piperidine ring, is very active in sexual behaviour tests in animals at doses much lower than compound (B), and that, unlike compound (B), it is completely inactive or rather poorly active as antidepressant/anxiolytic agent and completely devoid of neuroprotective/neurotrophic acitvity.

A first object of the present invention is therefore the compound of formula (I) above as well as the acid addition salts thereof.

The compound of formula (I) is in fact a basic compound which may form acid addition salts with various organic and inorganic acids.

While it is agreed that for its administration to animals and for the preparation of pharmaceutical compositions said salts must be pharmaceutically acceptable, it may be suitable to isolate from the reaction mixture the compound of formula (I) as an addition salt with an acid not pharmaceutically acceptable, converting it into the free base by treatment with an alkaline agent and optionally converting the thus obtained free base into a pharmaceutically acceptable acid addition salt.

Both pharmaceutically acceptable and unacceptable addition salts of compound (I) are therefore part of the present invention. They are easily prepared by treating the compound (I) as a free base, with at least an equimolar amount of the suitably selected inorganic or organic acid, in an aqueous or organic solvent, such as ethanol or isopropanol, followed by the evaporation to dryness of the solvent.

The acids which are useful for the preparation of the pharmaceutically acceptable acid addition salts of the compound (I) are those which form non toxic addition salts, i.e. those which contain anions which are pharmacologically acceptable, such as the hydrochloride, hydrobromide, hydroiodide, nitrate, sulfate, hydrogensulfate, phosphate, acetate, lactate, succinate, tartrate, fumarate, maleate, gluconate, D-glucarate, isethionate, methanesulfonate, p-toluenesulfonate, pamoate, angelate, etc.

The compound of formula (I) may be prepared according to any of the following methods:

(a) reaction of 4-(3-trifluoromethylphenyl)piperidine of formula (II)

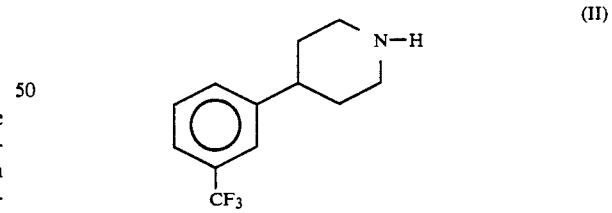

with a compound of formula (III)

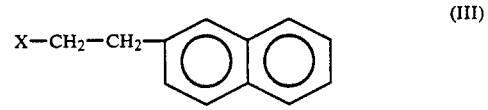

wherein X represents a chlorine, bromine or iodine atom or a leaving group such as methanesulfonyloxy or p-toluenesulfonyloxy group, optionally and preferably in the presence of a conventional base to neutralize the acid HX which forms during the reaction;

(b) reaction of 4-(3-trifluoromethylphenyl)piperidine of formula (II) with a functional derivative of the acid of formula (IV)

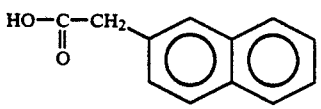

followed by reduction of the thus obtained intermediate; or (c) reduction of the double bond of the corresponding 1,2,3,6-tetrahydropyridine derivative of formula (B) above.

In preparation method (a), a polar organic solvent is preferably employed such as an alkanol of from 1 to 5 carbon atoms, e.g. methanol, ethanol, butanol or pentanol; a cyclic ether, e.g. dioxane or tetrahydrofuran; an aliphatic ketone, e.g. acetone, methyl ethyl ketone, methyl isobutyl ketone, etc; an alkyl sulfoxide, e.g. dimethylsulfoxide or diethylsulfoxide; or a dialkylamide, e.g. dimethylacetamide, or dimethylformamide, etc.

Preferably the reaction is carried out in the presence of a conventional base in an at least equimolar amount with respect to the acid which forms during the reaction. Said base may be an alkali metal carbonate or bicarbonate or an organic base such as an aliphatic tertiary amine, in particular triethylamine.

The reaction temperature may vary between room temperature and 200° C. and the reaction time will vary consequently. Generally, the reaction is complete in 4 to 5 hours at a temperature of from 100° to 150° C., and the thus obtained compound of formula (I) may be isolated according to conventional techniques and optionally converted into an acid addition salt thereof by simple salification.

In the first step of preparation method (b), the compound of formula (II) is reacted with a functional derivative of the acid (IV) wherein, as suitable functional derivative, the activated free acid, the anhydride, a mixed anhydride, an active ester, or an acyl halide, preferably the acyl chloride, is employed. Among the active esters, the p-nitrophenyl ester is particularly preferred but the methoxyphenyl, trytyl, benzhydryl, and the like esters can also be employed.

The temperature of the reaction may vary between −10° C. and the reflux temperature of the solvent employed, but generally the reaction is carried out at a temperature of from room temperature to 50° C. It may be convenient to carry out the reaction at low temperature when the reaction is exothermic, such as when the acyl chloride is used as functional derivative of the acid (IV).

As the reaction solvent, an alcohol, such as methanol or ethanol, or a halogenated solvent, such as methylene chloride, dichloroethane, chloroform and the like, is preferably employed, but other organic solvents compatible with the reactants, such as dioxane, tetrahydrofuran, or hydrocarbons, such as hexane, may be used as well.

The reaction may conveniently be carried out in the presence of a proton acceptor, for instance an alkali metal carbonate or a tertiary amine, when an acid forms during the reaction, but said proton acceptor is not necessary to obtain the intermediate amide.

If desired, this intermediate product may be isolated and characterised according to conventional techniques, otherwise it may also be employed, as a raw product, in the subsequent reduction step.

This latter step is performed according to known methods using aluminum hydride, or a lithium aluminum complex hydride such as $LiAlH_4$, $LiAlH(OCH_3)_3$ and the like, as the reducing agent. Generally the reaction is carried out in an inert solvent such as an ether, e.g. diethyl ether, tetrahydrofuran, dioxane, or 1,2-dimethoxyethane.

According to a preferred embodiment, the reaction is carried out using an equimolar amount of lithium aluminum hydride, $LiAlH_4$, with respect to the intermediate compound obtained in the former step, at a temperature of 20°–30° C. in diethyl ether and under inert atmosphere. After about 1 hour, the reduction reaction is complete and the compound of formula (I) is isolated according to conventional techniques as the free base or as one of its salts.

According to preparation method (c), the compound of formula (I) is easily prepared by catalytic hydrogenation, preferably using Pd/C as the hydrogenation catalyst and ethanol as the reaction solvent. The reaction may be performed at a temperature comprised between room temperature and the reflux temperature of the reaction solvent. When the hydrogenation reaction is complete, the catalyst is removed by filtration and the compound of formula (I) is obtained by evaporation of the solvent and crystallisation from a suitable solvent.

The starting compound of formula (II) is a known product, whose preparation has been described e.g. in European patent application EP-A-0 372 776, Preparation L.

Also the acid of formula (IV) and its functional derivatives are known in the open literature and compound (B), as anticipated, has been described in European patent EP-B-101 381.

In the following the preparation of the compound (I) by the method (c) is described as a non limitative example of preparation:

A mixture of 1-[2-(2-naphtyl)ethyl]-4-(3-trifluoromethylphenyl)-1,2,3,6-tetrahydropyridine hydrochloride (5 g, 0.012 mol), 10% Pd/C (0.6 g) and 95% ethanol (130 ml) are charged into a hydrogenation reaction vessel and hydrogenated, under stirring, at 50° C. for 3 hours. The catalyst is then removed by filtration and the filtrate is concentrated to dryness. The residue is triturated with a small amount of diethyl ether and the white solid which is obtained therefrom by filtration is crystallised from absolute ethanol (120 ml) and dried affording 3.5 g (0.0083 mol) of 1-[2-(2-naphthyl)ethyl]-4-(3-trifluoromethylphenyl)piperidine hydrochloride. M.p. 296°–298° C.

Starting from the thus obtained compound, by conversion into the corresponding free base followed by salification with the suitable acid, the corresponding fumarate, p-toluenesulfonate, succinate, L(+)-tartrate, and isethionate are prepared.

The compound of formula (I) of the present invention as well as the pharmaceutically acceptable acid addition salts thereof, tested in rats by the method described by A. Ågmo and Z. Picker in Pharmacol. Biochem. Behav., 1990, 35(2), 327-334 favourably modify the sexual behaviour of the test animals.

More particularly it has been found that the compound of formula (I), in rats, significantly increases male sexual motivation (evaluated as the number of mounts in a fixed time) as well as the intensity of the sexual behaviour of the male rat without sexual experience (affording a remarkable increase of the proportion of animals displaying mounts and intromissions as well as a similarly remarkable decrease in the ejaculation latency) at doses which do not elicit any anxiolytic/antidepressant or neurotrophic/neuroprotective activity.

The compound of formula (I) is also poorly toxic and can therefore be used as a medicament.

There may be envisaged, therefore, the use of the compound of formula (I) and of the pharmaceutically acceptable acid addition salts thereof in the treatment of sexual dysfunctions in mammals who suffer from such dysfunctions and are in need of a treatment thereof, or in the prevention of said dysfunctions, which comprises the administration of an effective amount of at least one of the compound of formula (I) and its pharmaceutically acceptable salts.

The compound of formula (I) and its pharmaceutically acceptable acid addition salts may be administered orally as well as parenterally.

Typically, the active principle according to the present invention is preferably administered at daily doses of from about 1.0 to about 200 mg, even if deviations may be necessary depending on the patient weight or condition, his individual response to the drug, the administration route, the type of pharmaceutical formulation and the treatment schedule.

The compound of formula (I) and its salts may be administered alone or admixed with pharmaceutically acceptable carriers and/or additives, by the oral or parenteral routes, according to treatment schedules which may comprise a single daily administration or several administrations per day.

More particularly, the new compound of formula (I) as well as its pharmaceutically acceptable salts may be administered in a variety of dosage forms: tablets, capsules, powders, suppositories, injectable suspensions or solutions, elixirs, syrups and the like.

The preferred administration route for the treatment of sexual dysfunctions is the oral route.

For this administration, an addition salt of the compound of formula (I) is preferably employed, it is admixed with additives and carriers conventionally used in the pharmaceutical industry and formulated as tablets, sugar-coated tablets, capsules, solutions or suspensions.

For the oral administration, compositions may be prepared using pharmaceutically acceptable vehicles such as microcrystalline cellulose, lactose, dicalcium phosphate, glycine, etc., optionally admixed with disintegrating agents, such as starch (maize, potato, tapioca starch, etc.), alginic acid, etc., dispersing or suspending agents, such as polyvinylpyrrolidone, sucrose, gelatin, etc. Furthermore, lubricating agents, such as magnesium stearate, talc, or sodium laurylsulfate, are often employed for the preparation of tablets. Tablets may also be treated so as to provide a delayed or sustained activity, and continuously release a predetermined amount of active principle.

Solid compositions as seen above may also be employed for the preparation of capsules and powders or granules dispersible in water.

A liquid composition in the form of a syrup or elixir or for the administration in drops, may contain the active principle in admixture with a sweetening agent, preferably calorie-free, methylparaben or propylparaben as antiseptics, as well as a flavouring agent and a suitable coloring agent, in a liquid vehicle.

The active principle may also be formulated as a microcapsule or microemulsion, optionally with one or more carriers or additives.

The active principle may also be encapsulated into a cyclodextrin (such as α or β-cyclodextrin) to increase its solubility.

For the parenteral administration, the pharmaceutical compositions of the present invention will contain the active principle in admixture with one or more aqueous or non-aqueous, pharmaceutically acceptable, sterile vehicles.

These pharmaceutical compositions may also contain additives such as suitable stabilizing, wetting, emulsifying, or dispersing agents.

The pharmaceutical compositions containing the compound of formula (I) or one of its pharmaceutically acceptable addition salts as the active principle, represent a further specific object of the present invention.

Particularly preferred are the pharmaceutical compositions containing from about 0.5 to about 100 mg of active principle per unit dosage form.

We claim:

1. A compound of formula (I)

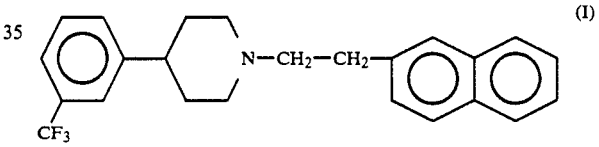

and its acid addition salts.

2. A compound according to claim 1 wherein the acid addition salts are pharmaceutically acceptable.

3. A pharmaceutical composition containing an effective amount of a compound of claim 2 mixed with a pharmaceutically acceptable carrier.

4. The composition of claim 3 which contains from about 0.5 to about 100 mg of active principle per unit dosage form.

5. A method of treating or preventing sexual dysfunctions which comprises administering to a mammal in need thereof an effective amount of a compound of formula (I)

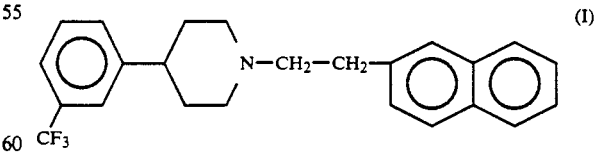

or a pharmaceutically acceptable salt thereof, or a mixture thereof.

* * * * *